(12) United States Patent
Maschmeyer et al.

(10) Patent No.: US 8,044,229 B2
(45) Date of Patent: Oct. 25, 2011

(54) ALICYCLIC POLYCARBOXYLIC ESTER MIXTURES WITH A HIGH TRANS PROPORTION AND METHOD FOR THE PRODUCTION THEREOF

(75) Inventors: Dietrich Maschmeyer, Recklinghausen (DE); Wilfried Bueschken, Haltern (DE); Michael Grass, Haltern (DE); Axel Tuchlenski, Muelheim (DE)

(73) Assignee: Evonik Oxeno GmbH, Marl (DE)

( * ) Notice: Subject to any disclaimer, the term of this patent is extended or adjusted under 35 U.S.C. 154(b) by 1401 days.

(21) Appl. No.: 10/490,028

(22) PCT Filed: Sep. 3, 2002

(86) PCT No.: PCT/EP02/09805
§ 371 (c)(1),
(2), (4) Date: Oct. 4, 2004

(87) PCT Pub. No.: WO03/029181
PCT Pub. Date: Apr. 10, 2003

(65) Prior Publication Data
US 2005/0038285 A1 Feb. 17, 2005

(30) Foreign Application Priority Data
Sep. 24, 2001 (DE) .................................. 101 46 869

(51) Int. Cl.
*C07C 69/74* (2006.01)
*C08G 63/02* (2006.01)
(52) U.S. Cl. ....................................... 560/127; 528/272
(58) Field of Classification Search .................. 560/127; 528/272
See application file for complete search history.

(56) References Cited

U.S. PATENT DOCUMENTS

| | | | |
|---|---|---|---|
| 2,070,770 A * | 2/1937 | Amend .......................... | 560/127 |
| 3,027,398 A | 3/1962 | Logan | |
| 3,205,278 A * | 9/1965 | Lapporte ...................... | 560/127 |
| 3,326,972 A | 6/1967 | Hans et al. | |
| 3,428,668 A | 2/1969 | Huelsmann et al. | |
| 4,666,588 A * | 5/1987 | Murphy ..................... | 208/251 H |
| 5,614,486 A * | 3/1997 | Giersch et al. .................. | 512/21 |
| 2004/0097773 A1 | 5/2004 | Beckmann et al. | |
| 2006/0036121 A1 | 2/2006 | Kaizik et al. | |
| 2006/0167151 A1 | 7/2006 | Grass et al. | |
| 2007/0060768 A1 | 3/2007 | Grass et al. | |

FOREIGN PATENT DOCUMENTS

| | | |
|---|---|---|
| DE | 199 27 978 | 12/2000 |
| DE | 19927978 | 12/2000 |
| EP | 0 005 737 | 12/1979 |
| EP | 0005737 | 12/1979 |

OTHER PUBLICATIONS

U.S. Appl. No. 11/911,691, filed Oct. 2007, Grass et al.*
U.S. Appl. No. 10/489,317, filed Mar. 18, 2004, Bueschken, et al.
U.S. Appl. No. 10/474,044, filed Oct. 15, 2003, Bueschken, et al.
U.S. Appl. No. 10/519,413, filed Jan. 6, 2005, Grass, et al.
U.S. Appl. No. 10/511,595, filed Nov. 2, 2004, Grass, et al.
U.S. Appl. No. 10/579,471, filed May 15, 2006, Zanthoff, et al.
U.S. Appl. No. 11/739,345, filed Apr. 24, 2007, Grass, et al.
U.S. Appl. No. 11/622,567, filed Jan. 12, 2007, Grass, et al.
U.S. Appl. No. 11/911,691, filed Oct. 16, 2007, Grass, et al.

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

The present invention relates to the preparation of alicyclic polycarboxylic esters by ring-hydrogenation of the corresponding aromatic polycarboxylic esters on a catalyst which comprises at least one metal from the triad iron, cobalt, nickel, and at least one metal of the IInd, IIIrd, IVth, Vth, and/or VIth transition group of the Periodic Table.

An alicyclic carboxylic ester mixture with a proportion above 10 mol % of the trans isomers.

The use of the alicyclic polycarboxylic ester mixtures.

Mixtures made from plastics and from alicyclic polycarboxylic ester mixtures.

21 Claims, No Drawings

ALICYCLIC POLYCARBOXYLIC ESTER MIXTURES WITH A HIGH TRANS PROPORTION AND METHOD FOR THE PRODUCTION THEREOF

The present invention relates to alicyclic polycarboxylic esters with high trans content, prepared by ring-hydrogenation of the corresponding aromatic polycarboxylic esters.

Alicyclic polycarboxylic esters, such as the esters of cyclohexane-1,2-dicarboxylic acid, are used as a component of lubricating oil and as auxiliaries in metalworking. They are also used as plasticizers for polyolefins, such as PVC.

For plasticizing PVC it is currently mainly esters of phthalic acid that are used, for example dibutyl, dioctyl, dinonyl, or didecyl esters. Since these phthalates have recently been described as hazardous to health, there is a risk that their use in plastics could become restricted. Alicyclic polycarboxylic esters, some of which have been described in the literature as plasticizers for various plastics, could then be available as replacements, although with a somewhat different performance profile.

The most economic route to preparation of alicyclic polycarboxylic esters in most cases is ring-hydrogenation of the corresponding aromatic polycarboxylic esters, for example of the abovementioned phthalates. Some processes for this purpose have been disclosed:

U.S. Pat. Nos. 5,286,898 and 5,319,129 describe a process which can hydrogenate dimethyl terephthalate on supported Pd catalysts doped with Ni or with Pt and/or with Ru, at temperatures of 140° C. or above and at a pressure of from 50 to 170 bar, to give the corresponding dimethyl hexahydroterephthalate.

DE 28 23 165 hydrogenates aromatic carboxylic esters on supported Ni, Ru, Rh, and/or Pd catalysts to give the corresponding alicyclic carboxylic esters at from 70 to 250° C. and from 30 to 200 bar. U.S. Pat. No. 3,027,398 discloses the hydrogenation of dimethyl terephthalate on supported Ru catalysts at from 110 to 140° C. and from 35 to 105 bar.

WO 00/78704 discloses a process for hydrogenating benzenepolycarboxylic esters to give the corresponding alicyclic compounds. Here, use is made of supported catalysts which comprise Ru alone or together with at least one metal of the Ist, VIIth, or VIIIth transition group of the Periodic Table and have 50% of macropores.

The ring-hydrogenation of aromatic polycarboxylic esters can produce at least two isomers with respect to the ring system and to the ester functions.

For example, the products from the hydrogenation of phthalic diesters (benzene-1,2-dicarboxylic diesters) are cis- and/or trans-cyclohexane-1,2-dicarboxylic diesters. The cis diester here is the isomer in which one ester group has axial (a) orientation and the other has equatorial (e) orientation. The trans compound is the isomer in which both ester groups have either axial (a, a) or equatorial (e, e) orientation.

Hydrogenation of isophthalic diesters (benzene-1,3-dicarboxylic diesters) can produce cis- and trans-cyclohexane-1, 3-dicarboxylic diesters. In the cis compound the esters groups have either axial-axial (a, a) or equatorial-equatorial (e, e) orientation. In the trans compound one ester group has axial orientation and the other has equatorial orientation.

The hydrogenation of terephthalic diesters (benzene-1,4-dicarboxylic diesters) can produce cis- and trans-cyclohexane-1,4-dicarboxylic diesters. Here, in the cis compound one ester group has axial orientation and the other has equatorial orientation (a,e). In the trans compound both ester groups have either axial (a,a) orientation or equatorial orientation (e,e).

In the case of alicyclic polycarboxylic esters having more than two substituents on the same ring system, each substituent can have cis or trans configuration with respect to another substituent. For the purposes of the present invention, all compounds in which the majority of the ester groups have transconfiguration with respect to one another are to be regarded as trans compounds, irrespective of the other configurations of the substituents with respect to one another.

The literature gives only sparse and incomplete information concerning the configuration of the products which are produced during the ring-hydrogenation of aromatic polycarboxylic esters.

For example, according to U.S. Pat. No. 3,027,165 the hydrogenation of dimethyl terephthalate on a ruthenium catalyst produces a mixture of dimethyl cis- and trans-cyclohexane-1,4-dicarboxylates with a melting point below 20° C. It is known that the melting point of the trans diester is 70° C. and that the melting point of the cis diester is 7° C. Assuming conventional melting behavior (no mixed crystal formation), i.e. that starting from one pure isomer and adding the other isomer, the melting point of the mixture falls until the eutectic point has been reached, it is possible to estimate that the hydrogenation mixture is composed mainly of dimethyl cis-cyclohexane-1,4-dicarboxylate.

S. Siegel and G. McCaleb in JACS, 81, 1959, pp. 3655-3658 describe the hydrogenation of dimethyl phthalates on suspended platinum oxide powder in glacial acetic acid. Irrespective of the pressure and concentration, the mixtures obtained of the corresponding cyclohexanoic acid derivatives have practically 100 mol % cis content.

The preparation of dimethyl cyclohexanedicarboxylates with high cis content is therefore known. However, that publication does not disclose whether other carboxylic esters with high cis content are accessible via the published method or any other method.

If the ruthenium-containing catalysts disclosed in WO 00/78704 are used for the hydrogenation of diisononyl phthalates, the product mixture obtained has about 93 mol % of cis isomer and correspondingly 7 mol % of the trans isomer.

The relevant literature gives no evidence of specifically prepared alicyclic polycarboxylic ester mixtures with increased content of the trans isomers.

It was therefore an object of the present invention to prepare mixtures of this type and to test their use as plasticizers.

Another object of the present invention was to develop a process which can hydrogenate aromatic polycarboxylic acids or esters of these and with which cyclohexanedicarboxylic compounds can be prepared with good selectivities and yields, without precious metal catalysts.

The invention therefore provides a process for the catalytic hydrogenation of aromatic polycarboxylic acids or derivatives of these using hydrogen, where the hydrogenation is carried out on a catalyst which comprises at least one metal from the triad iron, cobalt, nickel, together with at least one metal of the IInd, IIIrd, IVth, Vth and/or VIth transition group of the Periodic Table.

The invention therefore provides alicyclic polycarboxylic ester mixtures comprising at least two isomers with respect to the positioning of the ester groups on the ring system, the proportion of the trans isomers being above 10 mol %.

The alicyclic carboxylic esters of the invention (trans content>10%) have slightly lower volatility than the corresponding mixtures with lower trans content. This is significant particularly when they are to be used to manufacture plastics products for interior use.

Another effect of the lower volatility of these mixtures, which can be demonstrated by dynamic thermogravimetric analysis (TGA), for example, is that weight losses after heat-aging of plastics products are lower than when the plasticizers used are ester mixtures having lower trans contents. The performance of these mixtures is therefore superior to that of the conventional polycarboxylic ester mixtures.

The mixtures of the invention are preferably prepared by hydrogenation of the corresponding aromatic polycarboxylic esters. The catalyst systems mentioned below may in particular be used for this purpose.

Preferred metals of the IInd, IIIrd, IVth, Vth and/or VIth transition group are zinc and/or chromium. All of the catalysts used in the process of the invention may moreover also have an inert component (support) which comprises at least one metal selected from the group consisting of Al, Mg, Ti, Zr, and/or Si, in the form of oxide or mixed oxide. The catalysts may optionally also comprise salts of the abovementioned metals, for example sulfates and/or phosphates. The catalysts used according to the invention may also include processing and molding auxiliaries, such as graphite.

The formulations given below are based on the reduced catalysts.

The content of the metals mentioned of the VIIIth transition group (calculated as metal) in the catalysts is in the range from 1 to 60% by weight, in particular in the range from 25 to 45% by weight, very particularly from 30 to 40% by weight.

The content of metals of the IInd, IIIrd, IVth, Vth, and/or VIth transition group (calculated as oxide) in the catalysts is from 10 to 90% by weight, in particular from 20 to 60% by weight, very particularly from 20 to 40% by weight.

The process of the invention particularly preferably uses catalysts which in reduced, active form comprise at least some nickel in oxidation state 0 and zinc preferably in oxidation state +2.

The catalysts are prepared by processes known per se. One way of preparing a catalyst which comprises zinc oxide and nickel as main components and silicon dioxide as support is to precipitate nickel carbonate and zinc carbonate in a suspension of silica and, where appropriate, graphite in water. Other steps known to the skilled worker for preparation of the catalyst are: isolation and washing of the precipitate, drying, calcination, molding, and reduction.

It is advantageous to convert the catalysts into a form which offers small resistance to flow during the hydrogenation, for example tablets, cylinders, extrudates, or rings.

An example of a catalyst which may be used in the process of the invention is H10126 which can be purchased from Degussa AG, Dusseldorf, Germany. This catalyst has hitherto been used only for the hydrogenation of aromatic or olefinic hydrocarbons in halogen- and sulfur-containing raw materials. Its use for ring-hydrogenation of aromatic esters is not known. This catalyst comprises 32% by weight of nickel, 29% by weight of zinc oxide, and 24% by weight of silicon dioxide.

The hydrogenation in the process of the invention is preferably carried out in the liquid phase. The hydrogenation may be carried out continuously or batchwise on suspended catalysts or particulate catalysts in a fixed bed. In the process of the invention, preference is given to continuous hydrogenation on a fixed-bed arrangement of catalysts where the product/starting material phase is primarily in the liquid state under the conditions of the reaction.

If the hydrogenation is carried out continuously on a catalyst arranged in a fixed bed, it is advantageous to convert the catalyst into the active form prior to the hydrogenation. This may be achieved via reduction of the catalyst using hydrogen-containing gases, following a temperature program. This reduction may, where appropriate, be carried out in the presence of a liquid phase which trickles over the catalyst. The liquid phase used here may comprise a solvent or the hydrogenation product.

Differing versions of the process of the invention may be selected. It can be carried out adiabatically, polytropically, or practically isothermally, i.e. with a temperature rise typically smaller than 10° C., in one or more stages. In the latter case it is possible to operate all of the reactors, advantageously tubular reactors, adiabatically or practically isothermally, or else to operate one or more adiabatically and the others practically isothermally. It is also possible to hydrogenate the aromatic polycarboxylic esters in a straight pass or with product return.

The process of the invention is carried out in the mixed liquid/gas phase or liquid phase, cocurrently in three-phase reactors, the hydrogenation gas being distributed in a manner known per se within the liquid starting material/product stream. To promote uniform liquid distribution, improved dissipation of the heat of reaction, and high space-time yield, the reactors are preferably operated with high liquid flow rates of from 15 to 120, in particular from 25 to 80, $m^3$ per $m^2$ of cross section of the empty reactor per hour. If the reactor is operated with a straight pass, the liquid hourly space velocity (LHSV) over the catalyst may be from 0.1 to $10^{-1}$.

The hydrogenation may be carried out in the absence, or preferably in the presence, of a solvent. Solvents which may be used are any of the liquids which form a homogeneous solution with the starting material and product, exhibit inert behavior under hydrogenation conditions, and are easy to remove from the product. The solvent may also be a mixture of two or more substances and, where appropriate, comprise water.

Examples of substances which may be used as solvents are the following: straight-chain or cyclic ethers, such as tetrahydrofuran or dioxane, and also aliphatic alcohols whose alkyl radical has from 1 to 13 carbon atoms. Examples of alcohols which may preferably be used are isopropanol, n-butanol, isobutanol, n-pentanol, 2-ethylhexanol, nonanols, industrial nonanol mixtures, decanol, and industrial decanol mixtures, and tricedanols.

If alcohols are used as solvent it can be advantageous to use the alcohol or alcohol mixture which would be produced during saponification of the product (e.g. isononanol in the hydrogenation of diisononyl phthalate). This prevents any by-product formation via transesterification. Another preferred solvent is the hydrogenation product itself.

By using a solvent it is possible to limit the concentration of aromatic compounds in the reactor feed, and the result can be better temperature control achieved in the reactor. This can minimize side-reactions and therefore increase product yield. The content of aromatic compounds in the reactor feed is preferably from 1 to 35%, in particular from 5 to 25%. In the case of reactors operated in loop mode, the desired concentration range can be adjusted via the circulation rate (quantitative ratio of returned hydrogenation discharge to starting material).

The process of the invention is carried out in the pressure range from 30 to 250 bar, in particular from 50 to 100 bar. The hydrogenation temperatures are from 80 to 200° C., in particular from 100 to 140° C.

Hydrogenation gases which may be used are any desired hydrogen-containing gas mixtures in which there are no detrimental amounts present of catalyst poisons, such as carbon monoxide or hydrogen sulfide. Examples of the inert gas constituents are nitrogen and methane. It is preferable to use hydrogen at purity greater than 95%, in particular greater than 98%.

The process of the invention can convert aromatic polycarboxylic acids or derivatives of these, in particular their alkyl esters, to the corresponding alicyclic polycarboxylic compounds. In the case of the esters here, both full esters and partial esters can be hydrogenated. Full esters are compounds in which all of the acid groups have been esterified. Partial esters are compounds having at least one free acid group (or anhydride group) and at least one ester group. The process of the invention can, of course, also hydrogenate aromatic monocarboxylic esters to the corresponding alicyclic carboxylic esters.

The polycarboxylic esters of the invention and, respectively, the polycarboxylic esters prepared by the process of the invention preferably contain 2, 3, or 4 ester groups.

The polycarboxylic esters preferably used in the process of the invention are benzene-, diphenyl-, naphthalene- and/or anthracene polycarboxylic esters. The resultant alicyclic polycarboxylic esters are composed of one or more $C_6$ rings, where appropriate linked by a carbon-carbon bond or fused. Use may also optionally be made of polycarboxylic acids having an underlying diphenyl oxide skeleton.

The alcohol component of the polycarboxylic esters is preferably composed of branched or unbranched alkyl, cycloalkyl, or alkoxyalkyl groups having from 1 to 25 carbon atoms. These may be identical or different within one molecule of a polycarboxylic ester, i.e. they may be identical or different isomers or possess an identical or different number of carbon atoms.

In one preferred embodiment, the present invention provides a process for the hydrogenation of benzene-1,2-, -1,3-, or -1,4-dicarboxylic esters, and/or of benzene-1,2,3-, -1,3, 5-, , or -1,2,4-tricarboxylic esters, i.e. the mixtures of the invention comprise the isomers of cyclohexane-1,2-, -1,3-, or -1,4-dicarboxylic esters, or of cyclohexane-1 2,3-, -1,3,5-, or -1,2,4-tricarboxylic esters.

The following aromatic carboxylic acids may be used in the process of the invention: naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, phthalic acid (benzene-1,2-dicarboxylic acid), isophthalic acid (benzene-1,3-dicarboxylic acid), terephthalic acid (benzene-1,4-dicarboxylic acid), benzene-1,2,3-tricarboxylic acid, benzene-1,2, 4-tricarboxylic- acid (trimellitic acid), benzene-1,3,5-tricarboxylic acid (trimesic acid), benzene-1,2,3,4-tetracarboxylic acid, benzene-1,2,4,5-tetracarboxylic acid (pyromellitic acid). It is also possible to use acids which are produced from the acids mentioned by using alkyl, cycloalkyl, or alkoxyalkyl groups to substitute one or more of the hydrogen atoms bonded to the aromatic core.

It is possible to use alkyl, cycloalkyl, or else alkoxyalkyl esters of the abovementioned acids, these radicals encompassing, independently of one another, from 1 to 25, in particular from 3 to 15, very particularly from 8 to 13, particularly 9, carbon atoms. These radicals may be linear or branched. If a starting material has more than one ester group, these radicals may be identical or different.

Examples of compounds which may be used in the process of the invention as derivative of an aromatic polycarboxylic acid are the following: monomethyl terephthalate, dimethyl terephthalate, diethyl terephthalate, di-n-propyl terephthalate, dibutyl terephthalate, diisobutyl terephthalate, di-tert-butyl terephthalate, monoglycol terephthalate, diglycol terephthalate, n-octyl terephthalate, diisooctyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, ditridecyl terephthalate, di-n-octadecyl terephthalate, diisooctadecyl terephthalate, di-n-eicosyl terephthalate, monocyclohexyl terephthalate; monomethyl phthalate, dimethyl phthalate, di-n-propyl phthalate, di-n-butyl phthalate, diisobutyl phthalate, di-tert-butyl phthalate, monoglycol phthalate, diglycol phthalate, di-n-octyl phthalate, diisooctyl phthalate, di-2-ethylhexyl phthalate, di-n-nonyl phthalate, diisononyl phthalate, di-n-decyl phthalate, di-2-propylheptyl phthalate, diisodecyl phthalate, di-n-undecyl phthalate, diisoundecyl phthalate, ditridecyl phthalate, di-n-octadecyl phthalate, diisooctadecyl phthalate, di-n-eicosyl phthalate, monocyclohexyl phthalate, dicyclohexyl phthalate, monomethyl isophthalate, dimethyl isophthalate, diethyl isophthalate, di-n-propyl isophthalate, di-n-butyl isophthalate, diisobutyl isophthalate, di-tert-butyl isophthalate, monoglycol isophthalate, diglycol isophthalate, di-n-octyl isophthalate, diisooctyl isophthalate, 2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-dodecyl isophthalate, ditridecyl isophthalate, di-n-octadecyl isophthalate, diisooctadecyl isophthalate, di-n-eicosyl isophthalate, monocyclohexyl isophthalate.

It is also possible to use mixtures made from two or more polycarboxylic esters. Examples of mixtures of this type may be obtained in the following ways:
a) a polycarboxylic acid is partially esterified using an alcohol in such a way as to give both full and partial esters.
b) A mixture of at least two polycarboxylic acids is esterified using an alcohol, producing a mixture of at least two full esters.
c) A polycarboxylic acid is treated with an alcohol mixture, and the product can be a mixture of many full esters.
d) A polycarboxylic acid may also be partially esterified using an alcohol mixture.
e) A mixture of at least two carboxylic acids may also be partially esterified using an alcohol mixture.
f) A mixture of at least two polycarboxylic acids may also be partially esterified using an alcohol mixture.

Instead of the polycarboxylic acids in reactions a) to f), use may also be made of their anhydrides.

Aromatic esters are often prepared industrially from alcohol mixtures, in particular the full esters by route c).

Examples of corresponding alcohol mixtures are:
$C_5$ alcohol mixtures prepared from linear butenes by hydroformylation followed by hydrogenation;
$C_5$ alcohol mixtures prepared from butene mixtures which comprise linear butene and isobutene, by hydroformylation followed by hydrogenation;
$C_6$ alcohol mixtures prepared from a pentene or from a mixture of two or more pentenes, by hydroformylation followed by hydrogenation;
$C_7$ alcohol mixtures prepared from triethylene or dipropene or from a hexeneisomer or from some other mixture of hexeneisomers, by hydroformylation followed by hydrogenation;
$C_8$ alcohol mixtures, such as 2-ethylhexanol (2 isomers), prepared by aldol condensation of n-butyraldehyde followed by hydrogenation;
$C_9$ alcohol mixtures prepared from $C_4$ olefins by dimerization, hydroformylation, and hydrogenation. The starting materials here for preparing the $C_9$ alcohols may be isobutene or a mixture of linear butenes or mixtures of linear butenes and isobutene. The $C_4$ olefins may be dimerized with the aid of various catalysts, such as protonic acids, zeolites, organometallic nickel compounds, or solid nickel-containing catalysts. The $C_8$ olefin mixtures may be hydroformylated with the aid of rhodium catalysts or cobalt catalysts. There is therefore a wide variety of industrial $C_9$ alcohol mixtures.

$C_{10}$ alcohol mixtures prepared from tripropylene by hydroformylation followed by hydrogenation; 2-propylheptanol (2 isomers) prepared by aldol condensation of valeraldehyde followed by hydrogenation;

$C_{10}$ alcohol mixtures prepared from a mixture of at least two $C_5$ aldehydes by aldol condensation followed by hydrogenation;

$C_{13}$ alcohol mixtures prepared from hexaethylene, tetrapropylene, or tributene, by hydroformylation followed by hydrogenation.

Other alcohol mixtures may be obtained by hydroformylation followed by hydrogenation from olefins or olefin mixtures which arise in Fischer-Tropsch syntheses, in the dehydrogenation of hydrocarbons, in metalthesis reactions, in the polygas process, or in other industrial processes, for example.

Olefin mixtures with olefins of differing carbon numbers may also be used to prepare alcohol mixtures.

The process of the invention can use any ester mixture prepared from aromatic polycarboxylic acids and from the abovementioned alcohol mixtures. According to the invention, preference is given to esters prepared from phthalic acid or phthalic anhydride and from a mixture of isomeric alcohols having from 6 to 13 carbon atoms.

Examples of industrial phthalates which can be used in the process of the invention are products with the following tradenames:

Vestinol C (Di-n-butyl phthalate) (CAS No. 84-74-2); Vestinol IB (Diisobutyl phthalate) (CAS No. 84-69-5); Jayflex DINP (CAS No. 68515-48-0); Jayflex DIDP (CAS No. 68515-49-1); Palatinol 9-P (68515-45-7), Vestinol 9 (CAS No. 28553-12-0); TOTM (CAS No. 3319-31-1); Linplast 68-TM, Palatinol N (CAS No. 28553-12-0); Jayflex DHP (CAS No. 68515-50-4); Jayflex DIOP (CAS No. 27554-26-3); Jayflex UDP (CAS No. 68515-47-9); Jayflex DIUP (CAS No. 85507-79-5) Jayflex DTDP (CAS No. 68515-47-9); Jayflex L9P (CAS NO. 68515-45-7); Jayflex L911P (CAS No. 68515-43-5); Jayflex L11P (CAS No. 3648-20-2); Witamol 110 (CAS No. 68515-51-5); Witamol 118 (Di-n-C8-C10-alkyl phthalate) (CAS No. 71662-46-9); Unimoll BB (CAS No. 85-68-7); Linplast 1012 BP (CAS No. 90193-92-3); Linplast 13XP (CAS No. 27253-26-5); Linplast 610P (CAS No. 68515-51-5); Linplast 68 FP (CAS No. 68648-93-1); Linplast 812 HP (CAS No. 70693-30-0); Palatinol AH (CAS No. 117-81-7); Palatinol 711 (CAS No. 68515-42-4); Palatinol 911 (CAS No: 68515-43-5); Palatinol 11 (CAS No. 3648-20-2); Palatinol Z (CAS No. 26761-40-0); Palatinol DIPP (CAS No. 84777-06-0); Jayflex 77 (CAS No. 71888-89-6); Palatinol 10 P (CAS No. 53306-54-0); Vestinol AH (CAS No. 117-81-7).

Reference is made below to the possible stereoisomers of the alicyclic system, the trans form being differentiated from the cis form. For example, as mentioned above, in the case of cyclohexane-1,2-dicarbocylic esters the trans forms are the compounds in which the ester groups have either axial-axial (a,a) or equatorial-equatorial (e,e) orientation. In the cis compound one ester group has axial (a) orientation and the other has equatorial (e) orientation. As stated above, other orientations may apply for distinguishing between these two forms in the case of other alicyclic polycarboxylic acids.

The mixtures of the invention and, respectively, the mixtures prepared according to the invention comprise more than 10 mol %, based on the entire amount of ester, of trans compound(s). The mixtures preferably comprise more than 15 mol %, particularly preferably above 20 mol %, very particularly preferably above 25 mol %, of the trans isomer.

In particular versions of the process of the invention, dinonyl phthalates or a mixture made from isomeric dinonyl phthalates are hydrogenated to give an isomeric mixture of dinonyl cyclohexane 1,2-dicarboxylates with above 10 mol % content of the trans isomer with respect to the position of the carboxy groups on the cyclohexane ring.

By analogy, di(2-ethylhexyl) phthalate can similarly be converted to di(2-ethylhexyl) cyclohexane-1,2-dicarboxylate, or didecyl phthalate to didecyl cyclohexane-1,2-dicarboxylate. With regard to the cis/trans isomers, what has been said for the isononyl esters applies here.

For all of the classes of compounds mentioned, the content of the trans isomers in the resultant mixture can be above 15 mol %, preferably above 20 mol %, very particularly preferably above 25 mol %.

For example, in hydrogenating Vestinol 9 (diisononyl phthalate from Oxeno GmbH) according to the invention the content of trans compounds in the product is from 11 to 26% by weight, as can be determined by $^1$H NMR spectroscopy.

"Isomeric" phthalates is the term for the structural isomers resulting from the various radicals bonded to the oxygen atom of the ester group. For example, isomeric nonyl phthalates may contain n-nonyl radicals and also various singly or multiply branched radicals having 9 carbon atoms.

The present invention also provides the use of the alicyclic polycarboxylic ester mixture of the invention with high trans content as a plasticizer in plastics. Preferred plastics are PVC, homo- and copolymers based on ethylene, on propylene, on butadiene, on vinyl acetate, on glycidyl acrylate, on glycidyl methacrylate, on acrylates, or on acrylates having, bonded to the oxygen atom of the ester group, alkyl radicals of branched or unbranched alcohols having from one to ten carbon atoms, or on styrene or on acrylonitrile, and homo- or copolymers of cyclic olefins.

The following plastics may be mentioned as representatives of the above groups:

polyacrylates having identical or different alkyl radicals having from 4 to 8 carbon atoms, bonded to the oxygen of the ester group, in particular having the n-butyl, n-hexyl, n-octyl, or 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, and methyl methacrylate-styrene-butadiene copolymers.

The alicyclic polycarboxylic esters of the invention or the mixture may moreover be used to modify plastics mixtures, for example the mixture of a polyolefin with a polyamide.

The present invention also provides mixtures made from plastics with the alicyclic polycarboxylic ester mixtures of the invention, or prepared according to the invention. Suitable plastics are the abovementioned compounds. These mixtures preferably comprise at least 5% by weight, particularly preferably from 20 to 80% by weight, very particularly preferably from 30 to 70% by weight, of the alicyclic polycarboxylic esters.

Mixtures made from plastics, in particular PVC, and comprising alicyclic polycarboxylic ester mixtures of the invention, may be present in the following products, for example:

casings for electrical devices, such as kitchen appliances, computer cases, casings and components of phonographic and television equipment, of piping, of apparatus, of cables, of wire sheathing, of insulating tapes, of window profiles, in interior decoration, in vehicle construction and furniture construction, plastisols, in floor coverings, medical products, packaging for food or drink, gaskets, films, composite films, phonographic disks, synthetic leather, toys, containers for packaging, adhesive-tape films, clothing, coatings, and fibers for fabrics.

Mixtures made from plastics, in particular PVC, and comprising alicyclic polycarboxylic ester mixtures of the invention may moreover be used for producing the following products, for example:

a casing for electrical devices, piping, apparatus, a cable, wire sheathing, a window profile, a floor covering, a medical product, a toy, packaging for food or drink, a gasket, a film, a composite film, a phonographic disk, synthetic leather, a container for packaging, an adhesive-tape film, clothing, a coating, or a fiber for fabrics.

Besides the abovementioned applications, the alicyclic polycarboxylic ester mixtures of the invention may be used as a component in lubricating oil, or as a constituent of coolants or metal working fluids.

The examples below are intended to illustrate the invention without restricting the scope of protection defined by the patent claims.

Analysis

The ratio of cis- and trans-cyclohexane-1,2-dicarboxylic diesters was determined by $^1$H NMR spectroscopy.

Measuring device: Avance DPX-360 NMR spectrometer from the company Bruker
Measurement frequency: 360 MHz
Sample head: QNP sample head, 5 mm
Solvent: CDCl$_3$ (degree of deuteration 99.8%)
Standard: Tetramethylsilane (TMS)
Measurement temperature: 303 K
Number of scans: 32
Delay: 1 s
Acquisition time: 4.4 s
Spectral width: 7440.5 Hz
Pulse angle: 30°
Pulse length: 3.2 µs An example of the method of recording the $^1$H NMR spectra comprised dissolving about 20 mg of the specimen in about 0.6 ml of CDCl$_3$ (with 1 % by weight of TMS). The spectra were recorded under the conditions given above and referenced to TMS=0 ppm.

In the $^1$H NMR spectra obtained, the methyne signals for dialkyl cis- and trans-hexahydrophthalates could be distinguished with chemical shifts of about 2.8 ppm and 2.6 ppm, respectively, the signal shifted toward lower field corresponding to the cis compound (larger ppm value). To quantify the isomers, the integrals were determined from 3.0 ppm to 2.7(2) ppm and from 2.7(2) ppm to 2.5 ppm, the two integrals being separated in the middle between the signals. The ratio of the two isomeric structures could be determined from the intensity ratios.

The catalyst used was the commercially available H 10126 rs, produced by Degussa AG. The producer describes its properties as follows:

| | | |
|---|---|---|
| w(Ni) | about | 32% |
| w(ZnO) | about | 30% |
| w(SiO$_2$) | about | 24% |
| Form | Tablets | |
| Bulk density | about | 1.00 g/cm$^3$ |
| spec. pore volume | about | 0.4 cm$^3$/g |
| BET surface area | about | 160 m$^2$/g |

Activation Procedure for Reduction of the Oxidic Form of H 10126

The catalyst bed was heated to 250° C. in a stream of nitrogen. Once the O$_2$ content in the exhaust gas had fallen below 0.2%, hydrogen was slowly fed in to give an initial concentration of 5% by volume. The temperature in the catalyst bed was then increased by about 25° C./h to 350° C. Once the rate of formation of water produced during the reduction fell away, the hydrogen concentration was gradually raised to 100%. The temperature of from 300 to 350° C. was maintained for a further 36 hours in the stream of hydrogen. The hydrogen flow rate during the main reduction phase was 500 Nl/l/h. The activation was carried out at atmospheric pressure.

EXAMPLE 1

82 g of the Ni/Zn catalyst H 10126 were charged to a catalyst basket and carefully reduced in a stream of hydrogen, as specified by the producer, in a 600 ml pressure reactor, and then treated with 590 g of liquid diisononyl phthalate (Vestinol 9). The DINP was hydrogenated using pure hydrogen at a pressure of 200 bar and at a temperature of 120° C. After the starting material had been hydrogenated, the reactor was depressurized and the reaction mixture was analyzed. The DINP conversion was then 99.9%. The yield of di(isononyl) cyclohexane-1,2-dicarboxylate (DINCH) was 99.8%, the content of the cis compounds being 84% (determined via $^1$H NMR).

By analogy with example 1, further hydrogenation trials were carried out with the same catalyst. Pressures and temperatures were varied. The starting materials used comprised diisononyl phthalate (Vestinol 9) and di(2-ethylhexyl) phthalate (DOP). The trials were summarized in the table below.

| Example | Starting material | Pressure (bar) | Temperature (° C.) | Yield (%) | cis content (%) |
|---|---|---|---|---|---|
| 1 | Vestinol 9 | 200 | 120 | >99.8 | 84 |
| 2 | Vestinol 9 | 200 | 200 | >99.9 | 78 |
| 3 | Vestinol 9 | 50 | 200 | 99.8 | 74 |
| 4 | DOP | 50 | 200 | >99.9 | 71 |

What is claimed is:

1. An alicyclic polycarboxylic acid ester mixture, comprising:
at least two isomers of an alicyclic polycarboxylic acid ester whose structures are determined by the positions of the ester groups on the ring system of the ester compound, wherein the proportion of the trans isomers in the isomer mixture is above 10 mol %, the alicyclic polycarboxylic acid ester mixture being prepared by hydrogenating the corresponding aromatic polycarboxylic acid ester isomers over a catalyst which comprises at least one metal selected from the triad of elements consisting of iron, cobalt and nickel, together with at least one metal selected from the group consisting of the IInd, IIIrd, IVth, Vth and VIth transition group of the Periodic Table.

2. The alicyclic polycarboxylic acid ester mixture as claimed in claim 1, wherein the ring system is a compound of one or more C$_6$ rings.

3. The alicyclic polycarboxylic acid ester mixture as claimed in claim 1, wherein the polycarboxylic esters have 2, 3 or 4 ester groups.

4. The alicyclic polycarboxylic acid ester mixture as claimed in claim 1, wherein the alcohol components of the alicyclic polycarboxylic esters are alkoxyalkyl, cycloalkyl, and/or alkyl groups having from 1 to 25 carbon atoms, branched or unbranched, and in each instance identical or different.

5. The alicyclic polycarboxylic acid ester mixture as claimed in claim 1, wherein the alicyclic polycarboxylic ester mixture comprises the isomers of the cyclohexane-1,2-, 1,3-, 1,4-dicarboxylic acid esters, and/or of the cyclohexane-1,2,3-, 1,2,4- or 1,3,5-tricarboxylic acid esters.

6. A process for preparing alicyclic polycarboxylic acid esters, comprising:
hydrogenating an aromatic polycarboxylic acid ester isomer mixture in a mixed liquid/gas phase or liquid phase in three phase reactors in the presence of a catalyst which comprises at least one metal selected from the triad of elements consisting of iron, cobalt and nickel, together with at least one metal of the IInd, IIIrd, IVth, and/or Vth transition group of the Periodic Table, thereby preparing an alicyclic polycarboxylic acid ester isomer mixture that has a trans isomer content of greater than 10 mol %.

7. The process as claimed in claim 6, wherein the metal of the IInd, IIIrd, IVth, and/or Vth transition group of the Periodic Table comprises zinc and/or chromium.

8. The process as claimed in claim 6, wherein the catalyst further comprises an inert component.

9. The process as claimed in claim 8, wherein the inert component comprises at least one metal selected from the group consisting of Al, Mg, Ti, Zr and Si in the form of the oxides and/or mixed oxides.

10. The process as claimed in claim 6, wherein the content of iron, cobalt and/or nickel in the catalyst ranges from 1 to 60% by weight.

11. The process as claimed in claim 6, wherein the aromatic polycarboxylic acid ester is the alkyl, cycloalkyl or alkoxyalkyl ester of benzene-1,2-, 1,3-, 1,4-dicarboxylic acid, and/or of benzene-1,2,3-, 1,2,4- and/or 1,3,5-tricarboxylic acid.

12. The process as claimed in claim 6, wherein the alcohol components of the aromatic polycarboxylic esters are alkoxyalkyl, cycloalkyl and/or alkyl groups having from 1 to 25 carbon atoms, branched or unbranched, and in each instance identical or different.

13. The process as claimed in claim 6, wherein dinonyl phthalate or a mixture of isomeric dinonyl phthalates is hydrogenated to give an isomeric mixture of dinonyl cyclohexanedicarboxylates.

14. The process as claimed in claim 6, wherein decyl phthalate or a mixture of isomeric decyl phthalates is hydrogenated to give an isomeric mixture of decyl cyclohexanedicarboxylates.

15. The process as claimed in claim 6, wherein di(octyl) phthalate or a mixture of isomeric di(octyl) phthalates is hydrogenated to give an isomeric mixture of di(octyl) cyclohexanedicarboxylates.

16. The process as claimed in claim 13, wherein the hydrogenated mixtures have a proportion above 10 mol % of the trans isomers with respect to the position of the carboxy groups on the cyclohexane ring.

17. A mixture prepared from a plastic and the alicyclic polycarboxylic acid ester mixture as claimed in claim 1.

18. The mixture as claimed in claim 17, wherein the proportion of the alicyclic polycarboxylic acid ester in the mixture is at least 5% by weight.

19. A plastic, comprising: an alicyclic polycarboxylic acid ester mixture as claimed in claim 1.

20. The process as claimed in claim 6, wherein the three reactors are operated at liquid flow rates of 15 to 120 m$^3$ per m$^2$ per hour.

21. A process for preparing alicyclic polycarboxylic acid esters, comprising:
continuously hydrogenating an aromatic polycarboxylic acid ester isomer mixture over a fixed catalyst bed which comprises at least one metal selected from the triad of elements consisting of iron, cobalt and nickel, together with at least one metal of the IInd, IIIrd, IVth, and/or Vth transition group of the Periodic Table, thereby preparing an alicyclic polycarboxylic acid ester isomer mixture that has a trans isomer content of greater than 10 mol %.

* * * * *